(12) United States Patent
Reading (10) Patent No.: US 10,234,369 B2
(45) Date of Patent: Mar. 19, 2019

(54) METHOD AND APPARATUS FOR CHEMICAL MAPPING BY SELECTIVE DISSOLUTION

(71) Applicant: University of Huddersfield, Yorkshire (GB)

(72) Inventor: Michael Reading, Norfolk (GB)

(73) Assignee: University of Hudderfield, Leeds (GB)

( * ) Notice: Subject to any disclaimer, the term of this patent is extended or adjusted under 35 U.S.C. 154(b) by 80 days.

(21) Appl. No.: 15/119,635

(22) PCT Filed: Feb. 13, 2015

(86) PCT No.: PCT/GB2015/050417
§ 371 (c)(1),
(2) Date: Aug. 17, 2016

(87) PCT Pub. No.: WO2015/124906
PCT Pub. Date: Aug. 27, 2015

(65) Prior Publication Data
US 2017/0059465 A1    Mar. 2, 2017

(30) Foreign Application Priority Data
Feb. 20, 2014 (GB) .................. 1402965.6

(51) Int. Cl.
*G01N 13/00* (2006.01)
*G01N 30/06* (2006.01)
(Continued)

(52) U.S. Cl.
CPC ......... *G01N 13/00* (2013.01); *G01N 21/3577* (2013.01); *G01N 30/06* (2013.01);
(Continued)

(58) Field of Classification Search
CPC ........... G01N 21/05; G01N 2021/0339; G01N 2021/0342; G01N 2021/754;
(Continued)

(56) References Cited

U.S. PATENT DOCUMENTS

2005/0003550 A1* 1/2005 Kyne .................... G01N 33/15
436/2
2008/0138261 A1* 6/2008 Bogner .................. G01N 21/05
422/266
(Continued)

FOREIGN PATENT DOCUMENTS

WO        2006108908        10/2006

OTHER PUBLICATIONS

PCT/GB2015/050417 International Preliminary Report dated Sep. 13, 2016.
(Continued)

*Primary Examiner* — Paul M. West
(74) *Attorney, Agent, or Firm* — Nyemaster Goode, PC (57) ABSTRACT

An apparatus and method of analysis including at least one microscope means operable to characterize the surface of a sample in use, at least a first conduit to convey one or more solvents to the sample and a further conduit to convey at least part of the solution from the sample. At least one pump means delivers solvent to the sample and/or removes solution from the same.

3 Claims, 13 Drawing Sheets

(51) Int. Cl.
　　　　*G01Q 30/04*　　　　(2010.01)
　　　　*G01Q 30/14*　　　　(2010.01)
　　　　*G01Q 30/20*　　　　(2010.01)
　　　　*G01Q 60/24*　　　　(2010.01)
　　　　*G02B 21/00*　　　　(2006.01)
　　　　*H01J 37/26*　　　　(2006.01)
　　　　*G01N 21/3577*　　　(2014.01)

(52) U.S. Cl.
　　　　CPC ............ *G01Q 30/04* (2013.01); *G01Q 30/14* (2013.01); *G01Q 30/20* (2013.01); *G01Q 60/24* (2013.01); *G02B 21/00* (2013.01); *H01J 37/261* (2013.01); *G01N 2201/12* (2013.01)

(58) Field of Classification Search
　　　　CPC .......... G01N 2021/755; G02B 21/0016; G02B 21/0028; G01Q 30/14; G01Q 30/20
　　　　See application file for complete search history.

(56) References Cited

U.S. PATENT DOCUMENTS

2012/0079894 A1　　4/2012　Van Berkel
2012/0217192 A1*　8/2012　Blank .................. B01D 15/166
　　　　　　　　　　　　　　　　　　　　　　　　　　210/143

OTHER PUBLICATIONS

In Situ dissolution analysis.
Chemical Imaging of oral Solid Dosage Froms.
Dissolution on Cholesterol Monohydrate.
WO2015124906 Written Opinion.

* cited by examiner

METHOD AND APPARATUS FOR CHEMICAL MAPPING BY SELECTIVE DISSOLUTION

The present invention relates to an apparatus and method of using the same to record the dissolution of one or more compounds.

It is well know that methods of chemical imaging such as IR microscopy, Raman microscopy, Secondary Ion Mass Spectroscopy provide highly valuable information in a wide range of applications. However, these methods typically have limitations in terms of their scale of scrutiny, the amount of information they provide and the types of environment in which the sample can be placed. Furthermore, their analytical power is limited because each instrument provides only one kind of analysis and cannot be used with chromatography. Another drawback is that they all have limits in terms of their sensitivity for components present in low concentrations.

It is therefore an aim of the present invention to provide an apparatus that addresses the abovementioned problems.

It is a further aim of the present invention to provide a method that addresses the abovementioned problems.

In the first aspect of the invention there is provided an apparatus comprising at least one microscope means operable to characterize the surface of a sample in use, at least a first conduit to convey one or more solvents to the sample, and a further conduit to convey at least part of the solution from the sample wherein at least one pump means delivers solvent to the sample and/or removes solution from the same.

It is to be understood that the word solvent can mean a mixture of two or more solvents and/or entrainers. Furthermore, the one or more solvents can include species or compounds already substantially dissolved, or at least partially dissolved therein. The term solvent can also include a suspension for the purposes of the invention.

Typically the solvent and/or solution is a fluid. Further typically the fluid is a liquid.

Preferably the further conduit conveys at least part of the solution to at least one further instrument. Typically the further instrument is an analysis means capable of analyzing the at least part of the solution and/or one or more solutes contained therein.

Typically the analysis means includes any one or any combination of spectroscopic analysis, chromatographic analysis and/or the like. In one embodiment the analysis means is a HPLC-MS (high performance liquid chromatography-mass spectrometry) instrument.

Thus the present invention provides an apparatus arranged to measure changes in the surface of the sample as material is dissolved by the solvent and to analyze the solutes.

Typically analysis of the one or more solutes provides data that can be processed using suitable software to identify the chemical composition of components of the sample and/or locate their positions within and/or upon the sample.

In particular the chemical composition of components of the sample and/or their positions within and/or upon the sample can be determined even when more than one solute or component dissolves concurrently during the addition of solvent, in the course of the process, method or experiment.

In one embodiment the apparatus includes at least one sample location means.

In use, the sample is provided or placed substantially on a sample location means. Preferably the temperature of the sample location means is controlled and/or maintained at a predetermined temperature.

In one embodiment the sample location means includes a chamber. Typically the environment inside the chamber is temperature controlled. In one embodiment any one or any combination of atmospheric composition, humidity, light intensity and/or the like of the sample location means can be controlled and/or set to predetermined level.

Typically one or more of the sample location means parameters, such as temperature, is set and/or controlled by a computer means and/or one or more microprocessor means.

Typically the sample includes one or more compounds or materials. In one embodiment the sample includes different morphologies, isomers and/or enantiomers of a compound or material.

In one embodiment the one or more solvents dissolve at least part of the sample.

In a preferred embodiment a first pump means controls delivery of the solvent to the sample and a second pump means removes at least part of the solution. Typically the apparatus includes one of more reservoir means containing solvent in use.

In one embodiment the pump means controls the composition of the solvent delivered to the sample by mixing the content of two or more reservoir means.

Typically the microscope means includes optical (light) microscopes, electron microscopes and scanning probe microscopes. In one embodiment the microscope is an atomic force microscope (AFM).

In one embodiment the solution is conveyed to an instrument capable of analyzing the solutes via the intermediate step of collecting a sequence of aliquots in vessels.

In one embodiment the solution is conveyed directly to an instrument that can analyze the solutes.

In one embodiment the temperature of the sample is controlled to be an increasing monotonic function of time.

In one embodiment the temperature of the sample is controlled to be a combination of a monotonic function of time and a periodic function of time.

In one embodiment the composition of the solvent is controlled to be a monotonic function of time.

In one embodiment the composition of the solvent is controlled to be a combination of a monotonic function of time and a periodic function of time.

In a second aspect of the invention there is a method of identifying the chemical composition of one or more of the components of a sample and locating their positions within and/or upon the sample, said method comprising the steps of;

locating the sample within the field of view of at least one microscope means suitable for characterizing changes that occur in a sample as a consequence of its components being dissolved, conveying at least one solvent to the sample, and conveying at least part of the solution away from the sample.

Preferably the method includes the further step of analyzing the solutes. Typically analysis of the images produced by the microscope is performed, so that the location and/or quantity of material dissolved as a function of time can be estimated. Further typically different components are differentiated on the basis of their dissolution kinetics.

In one embodiment the data acquired with the microscope is correlated with the solute analytical data. Typically a map is created of how different components of the sample are spatially distributed within and/or upon the sample, even when more than one component dissolves concurrently during the course of the process and/or addition of solvent.

Preferably the composition of the solvent is capable of being controlled by a computer. Typically the one or more pump means are computer controlled.

Preferably the temperature of the sample and solvent surrounding it is controlled by a computer.

In one embodiment the sample remains within the field of view of the microscope as the sample is exposed to the solvent.

In an alternative embodiment the sample is removed from the field of view of the microscope and exposed to the solvent before the sample is returned to the field of view of the microscope. Typically this series is repeated multiple times. Further typically the series is repeated with different solvents and/or at different temperatures.

In one embodiment aliquots or discreet samples of the solution are collected for analysis.

In a third aspect of the invention there is provided an apparatus comprising at least one microscope operable to characterize the surface of a sample, at least one conduit to convey a solvent to the sample so that it can dissolve parts of the sample, a pumping system operable to control the composition of a solvent conveyed to the sample, a temperature controlled chamber within which the sample is located, a further conduit to convey the solution away from the sample to at least one instrument capable of analyzing the solutes; the apparatus being arranged to measure changes in the surface of the sample as material is dissolved by the solvent and to analyze the solutes thereby to provide data that can be processed using suitable software to identify the chemical composition of components of the sample and locate their positions within and/or upon the sample even when more than one component dissolves concurrently during the course of the experiment.

In a further aspect of the invention there is provided a method of identifying the chemical composition of the components of a sample and locating their positions within and/or upon the sample comprising placing the sample within the field of view of a microscope that can characterize changes that occur in a sample as a consequence of its components being dissolved, conveying the solvent to the sample so that it can dissolve parts of the sample, conveying the solution away from the sample, analyzing the solutes, analyzing the images produced by the microscope so that the location and quantity of material dissolved as a function of time are estimated and different components are differentiated on the basis of their dissolution kinetics, correlating the data acquired with the microscope with the analytical data thereby to create a map of how different components of the sample are spatially distributed within and/or upon the sample even when more than one component dissolves concurrently during the course of the experiment.

Parallel methods or processes may be performed without the microscope that are substantially the same with respect to the temperature of the sample, the composition of the solvents and the ratio of the volume of the solvent to the mass of the sample but with a larger sample than that used in the process conducted with the microscope. The data obtained by analyzing the solutes in the parallel methods are correlated with the images acquired by the microscope thereby to create a map of how different components of the sample are spatially distributed within and/or upon the sample.

In one embodiment the method includes the step of collecting aliquots of the solution for subsequent analysis.

In one embodiment the method includes the step of conveying the solution directly to an instrument capable of analyzing the solutes.

In one embodiment the method includes a parallel method or process that is conducted without the microscope but in substantially the same way with respect to the temperature of the sample, the composition of the solvents and the ratio of the volume of the solvent to the mass of the sample but with a larger sample than that used in the method or process conducted with the microscope; the data obtained by analysing the solutes in the parallel process being correlated with the images acquired by the microscope thereby to create a map of how different components of the sample are spatially distributed within and/or upon the sample.

In one embodiment the method includes the step of controlling the temperature of the sample to be an increasing monotonic function of time.

In one embodiment the method includes the step of controlling the temperature of the sample to be a combination of a monotonic function of time and a periodic function.

In one embodiment the method includes the step of controlling the composition of the solvent to change as a monotonic function of time.

In one embodiment the method includes the step of controlling the composition of the solvent to change as a combination of a monotonic function of time and a periodic function.

Specific embodiments of the invention are now described with reference to the following figures wherein.

What is proposed is a novel method of chemical mapping that can provide multiple types of analysis, including chromatography, down to the nanoscale.

The invention overcomes the limitations of current methods by combining:—

A type of microscopy that can characterize the removal of material from the surface of a sample including the removal of some domains more than others.

A means of conveying solvent to the sample so that material is dissolved from its surface.

A means of controlling the composition of the solvent so that it preferentially dissolves one material compared to another.

A means of controlling the temperature of the sample and solvent thereby to influence the rate at which materials are dissolved.

A means of collecting aliquots of the solution so that they can be analyzed and/or a direct link to an instrument that can analyze the solutes.

A means of correlating the measurements from the microscopy with the analytical results so that the location from which analytes were dissolved can be determined.

Figure 1A:
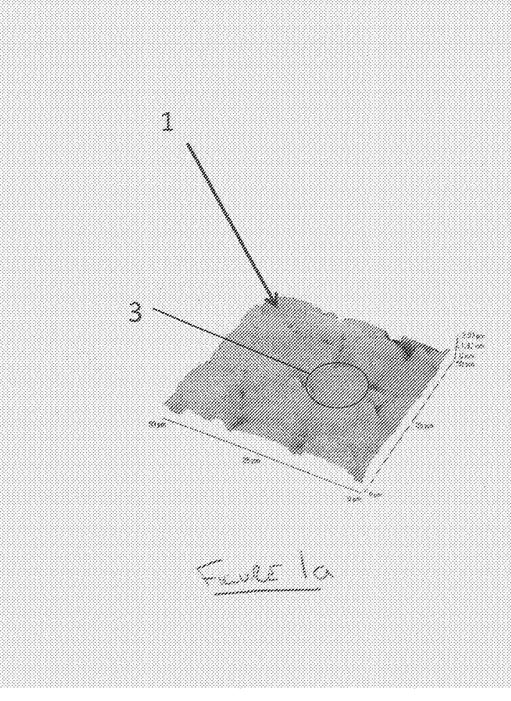
FIGS. 1a and 1b show AFM images of a sample of 30% Cyclosporin in HPMC before and after the sample has been immersed in dichloromethane.
Figure 1B:
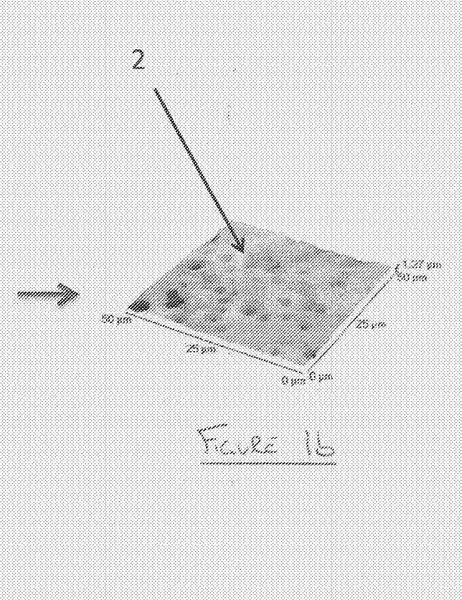

FIGS. 1a and 1b show an AFM image 1, 2 of a sample of 30% Cyclosporin in HPMC. The image 2 in FIG. 1b shows the sample after immersion in dichloromethane. Cyclosporin is soluble in dichloromethane, HPMC is not. The conclusion is the circular domains on the surface 3, are made up of the drug. This provides an example of how the use of a selective solvent can identify the composition of surface features. An analysis of the solution and solutes therein by, for example, HPLC-MS would enable the composition of the dissolved objects to be determined if this is not known in advance.

An important point is that analyzing material on the scale of nanometers is usually not done with intention of characterizing a single domain. For example, if it is considered to be important to analyze specifically domain 3 in FIG. 1 because it is the only domain with a given composition then this would not normally be feasible because it would be impossible to find just one nanometer sized object on a typical sample. Nanometric characterization usually only makes sense if it is the case that the area examined is representative of a much larger area. This is a requirement for the proposed method to work; however, this is a condition that would normally be met without difficulty; that it is met can be experimentally confirmed when necessary.

The simple process described above cannot be a general method of analysis because it cannot be routinely assumed that only one component is soluble in a given solvent. The picture is further complicated because the rate at which an object dissolves depends not only on how soluble it is but also by the size of the object that is dissolving. These complications can be addressed using any type of microscopy that can provide information about how different parts of a sample are dissolving combined with chemical analysis of the solutes and a suitable mathematical analysis to correlate the data from the microscope with the data from the methods of chemical analysis. For such a technique to be capable of analyzing a wide variety of samples it must be able to cope with the possibility that different components can dissolve concurrently; this can be achieved by determining the kinetics of dissolution at different points on the sample surface and differentiating between components on the basis of these kinetics.

Figures 2, 2A, 2B, 2C:
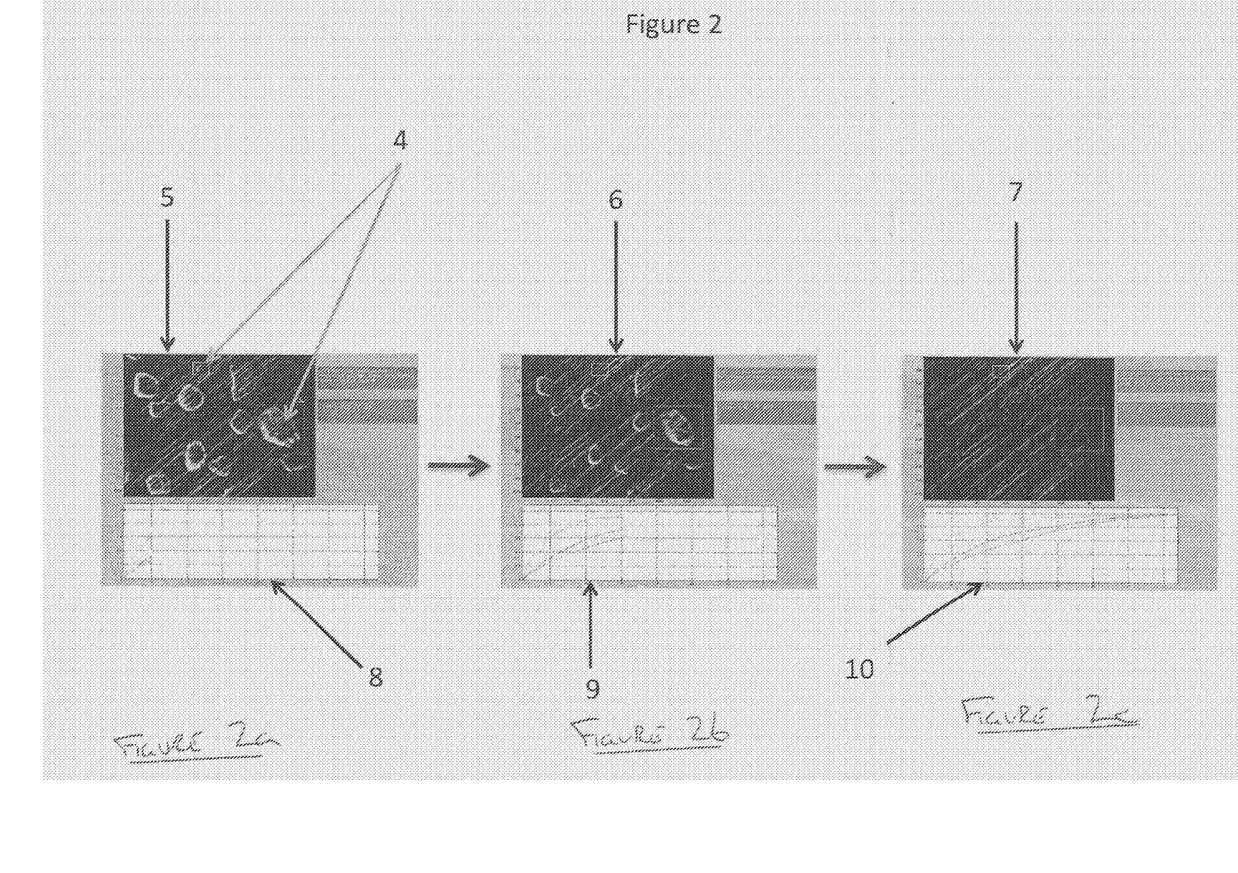
FIGS. 2a-2c show a series of screenshots providing of images of domains of a material dissolving in a solvent, and plots underneath the images detailing how selected domains become smaller.

FIGS. 2a-2c gives an example of how microscopy can be used to characterize the kinetics of dissolution by showing the images 5, 6 and 7 that were taken at the start 5, middle 6 and end 7 of the dissolution process. There is a distribution of particle sizes exemplified by 4; however, larger objects reduce in size so they all ultimately follow similar paths. There are a variety of image analysis algorithms that can be used to follow the process of dissolution including boundary recognition algorithms that track the reduction in size of the periphery of each object, information theory algorithms that track how the structure changes, statistical algorithms that track changes in pixel intensity and others known to those of ordinary skill in the art. Graphs 8, 9, 10 show the dissolution of the imaged objects as a function of time and/or addition of solvent.

Comparisons between objects can be made that differentiate between materials on the basis of the kinetics of dissolution; this is illustrated in FIG. 3. We have micrograph 11, in FIG. 3a, that images the domains 12. The dissolution of these domains is followed using the procedure illustrated in FIG. 2. The half-life (the time taken for the domain to reduce by half) of each domain is measured and plotted against the size of the domain. Domains that have the same kinetics of dissolution will all fall on the same monotonic curve; FIG. 3b shows the graph 13 including two populations 14 and 15 with different dissolution kinetics. Each domain from micrograph 11 can be allocated to the appropriate population and the total amount of material dissolved for that population can be calculated; this is plotted in graph 16, shown in FIG. 3c, as two normalized curves 17 and 18. The chromatograph 19, shown in FIG. 3d, taken of the solution sampled at the end of the experiment shows two peaks 20 and 21. In FIG. 3e, graph 22 shows the normalized peak heights 23 and 24 from aliquots of the solution taken during the course of the experiment are plotted.

Figure 3A:
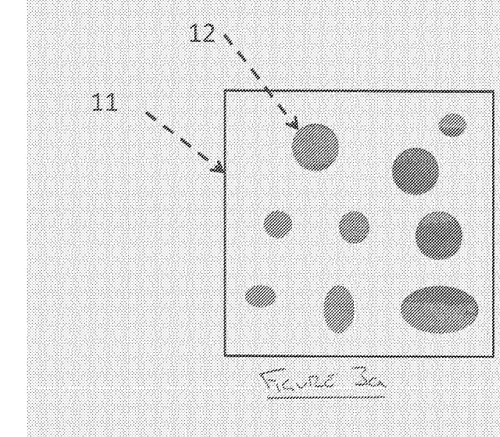
FIGS. 3a-3e show a series of schematic representations of data obtained using one embodiment of the invention applied to a sample with two soluble phases embedded in an insoluble matrix.
Figure 3B:
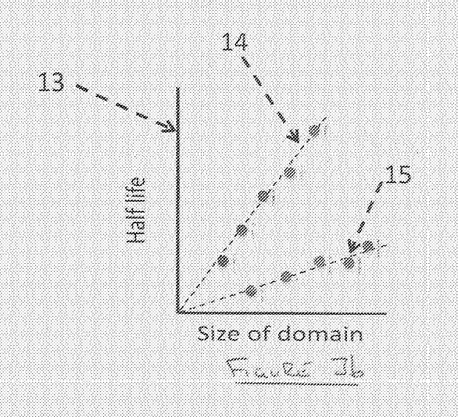
Figure 3C:
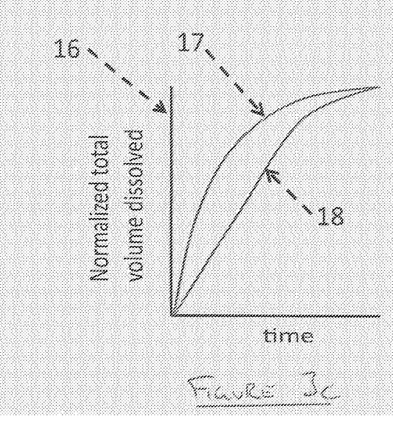
Figure 3D:
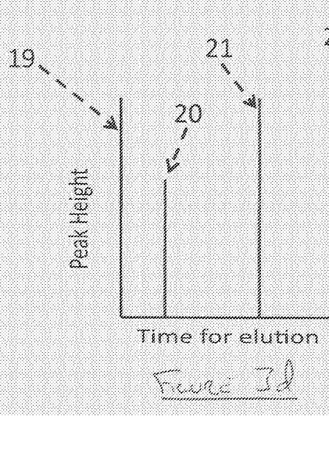
Figure 3E:
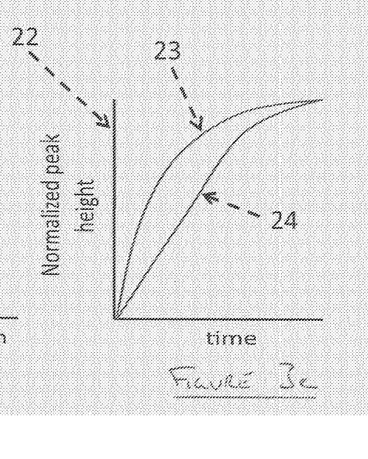

In this case simple inspection is sufficient to show that peak 20 corresponds to population 15 and peak 21 corresponds to population 14 thus the composition of each domain is determined and the distribution of the different materials can be mapped. In other cases inspection will not be sufficient, in these cases more sophisticated methods can be used such as algebraic determination of unknowns when sufficient knowns are available, multivariate statistical models, a wide variety of other techniques generally grouped under the heading chemometrics and other methods known to one of ordinary skill in the art.

This same principle can be applied to all other types of chemical analysis. It is possible to acquire IR spectra from aliquots of the solution then further analyze these aliquots using Raman spectroscopy or mass spectroscopy or a combination of all of these. In this way a great deal of analytical information can be acquired from a single imaging experiment, far more than can be obtained using conventional techniques.

The solvent can be made to flow over the sample in a continuous stream with a constant composition or the composition can be progressives changed by a pumping system that mixes different solvents. The solvent can be delivered as a series of pulses that may be separated by, for example, air or a liquid immiscible with the solvent. The temperature of the sample can be held constant or can be changed in a programmed fashion such as, but not limited to, a linear function with time. All of these variables can be changed in a monotonic manner or modulated to follow a periodic function such as a step function or a sine wave; these different types of monotonic and periodic functions can be used in combination. Varying the composition of the solvent and the temperature in the ways described above can improve the ability to discriminate phases on the basis of their different kinetics of dissolution and optimize the experiment by, for example, reducing the total time taken to complete it. Modulating the temperature may provide modulations in the rate of dissolution that can be analyzed by, for example, curve fitting techniques using periodic functions thereby improving sensitivity. Implementing periodic changes in solvent composition from one that preferentially dissolves one phase to one that preferentially dissolves another phase can make discriminating between these phases easier by using, for example, a discrete Fourier transform. A linear temperature ramp can ensure that an experiment does not take too long because one phase dissolves very slowly at room temperature. The options for varying temperature and solvent composition to improve performance are many and are not limited to the examples given above.

An approach that can increase the limit of detection is to carry out parallel experiments; one with the microscope using a small sample and another using a large sample without the microscope. Both experiments must be substantially the same with respect to the temperature of the sample, the composition of the solvents and the ratio of the volume of the solvent to the mass of the sample. Large amounts of analytes can be obtained from the large sample thus providing high sensitivity and this sample can be substantially larger than the one that can be accommodated by the microscope. However, provided the structure and composition of both samples are the same then the analytical data from the larger sample can be used with the images from the microscope to map the components of the sample in the same way as when the analytical data and the micrographs are obtained from the same sample. Data from parallel experiments using more than one form of microscopy can be used together.

These principles can be applied to the nanoscale using atomic force microscopy and electron microscopy as well as larger scales using optical microscopy, optical profiling and other methods capable of characterizing the surface of a sample.

Figure 4:
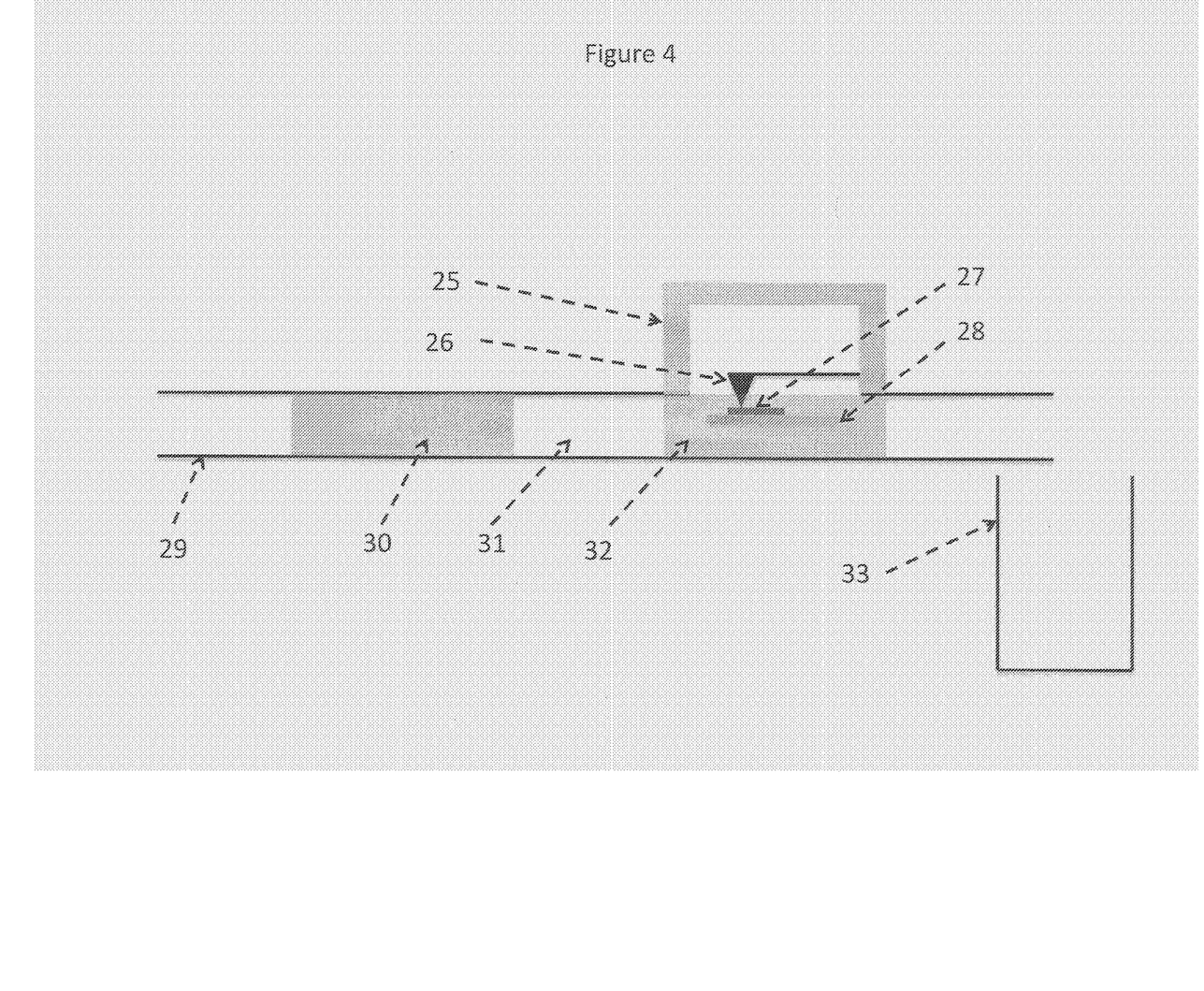
FIG. 4 shows a diagram of an apparatus that allows pulses of solvent to be delivered to a sample as it is being imaged using an atomic force microscope in accordance with one embodiment of the invention.

FIG. 4 shows a piece of apparatus (just one of a number of designs) that can characterize how material is removed from the surface of a sample 27 using a probe 26 actuated by an atomic force microscope 25. In this figure 'pulses' of different solvents 30 and 32 separated by an air gap 31 are conveyed along a tube to the sample 27. The atomic force microscope 25 characterizes the surface of the sample as the solvent dissolves part of the surface. The solvent 32 is then conveyed to vessel 33 for collection and subsequent analysis by a variety of means, for example IR spectroscopy or chromatography. At the same time solvent 30 is conveyed to the sample. This is just one design, many others embodiments can be constructed by one of ordinary skill in the art once the principles of the invention are understood.

The proposed method and apparatus introduce a new paradigm for chemical imaging. It can be used with any of the standard analytical techniques including chromatography thereby providing a step-change improvement in analytical discrimination compared to more conventional approaches. It can operate at the nanometer scale and above.

Figure 5A:
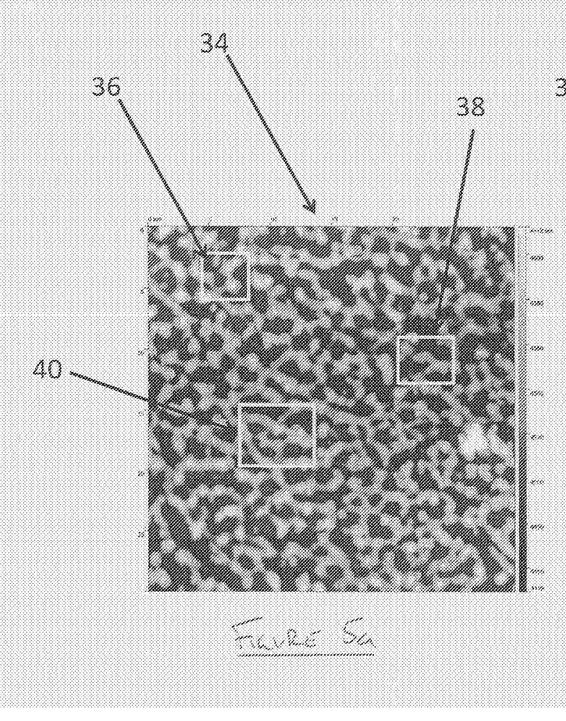
FIGS. 5a and 5b show two AFM images representing the topography of a two-phase sample before and after exposure to a solvent. Three areas are highlighted that are then analyzed in detail.
Figure 5B:
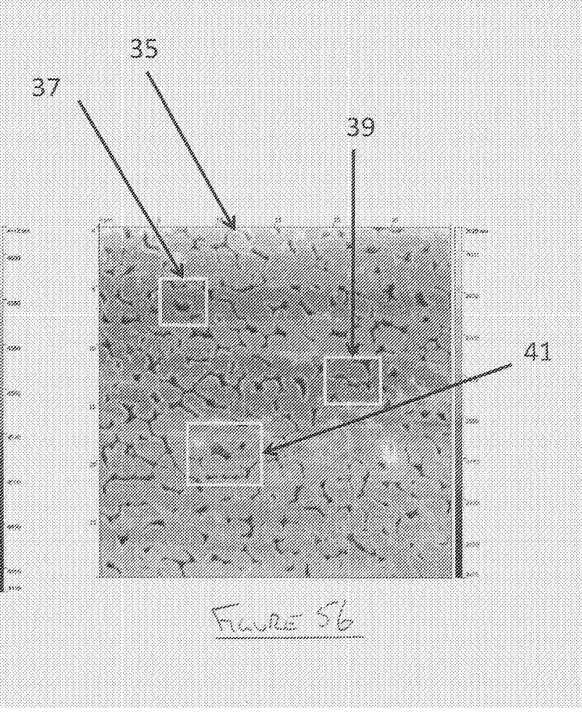
Figure 6:
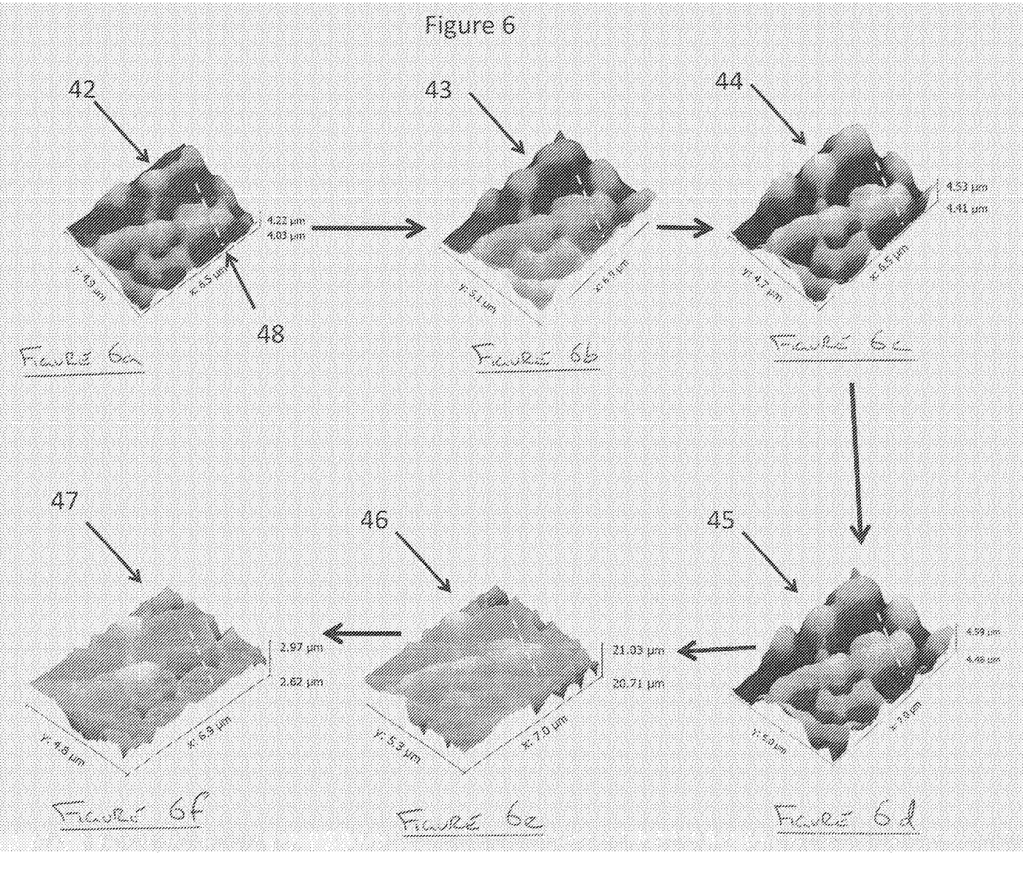
FIGS. 6a-6f show a succession of topographic maps as the sample is exposed to a series of immersions in a solvent according to the areas highlighted in FIG. 5, whereby one line scan over a selected feature is illustrated.
Figures 7A, 7B, 7E, 7F:
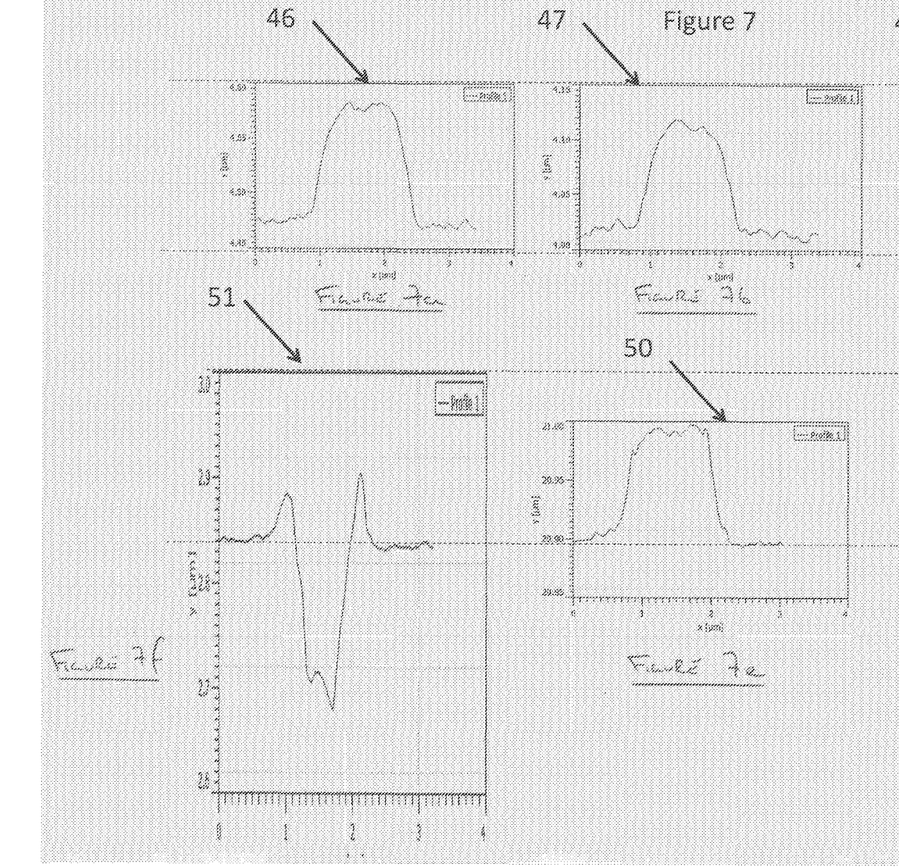
FIGS. 7a-7f show the results of the line scan highlighted in FIG. 6 whereby a succession of height profiles are produced as the sample is exposed to a series of immersions in a solvent.
Figure 7C:
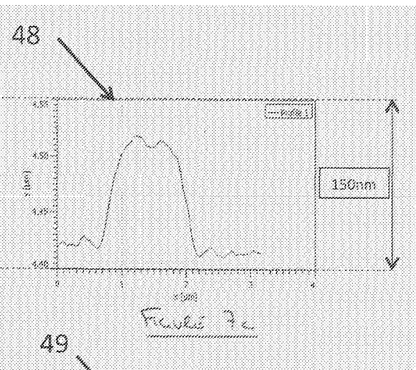
Figure 7D:
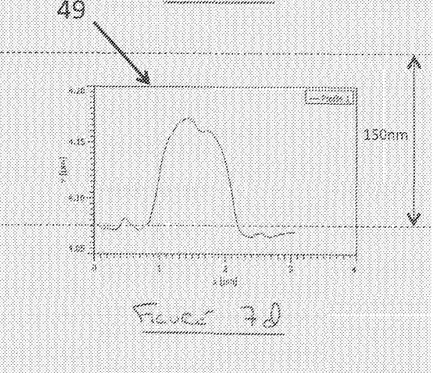
Figure 8A:
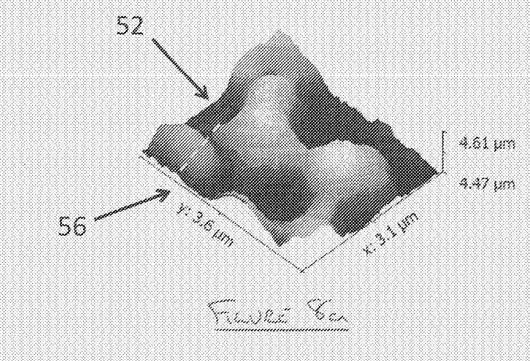
FIG. 8a-8d show a succession of topographic maps as the sample is exposed to a series of immersions in a solvent according to the areas highlighted in FIG. 5, whereby one line scan over a selected feature is illustrated.
Figure 8B:
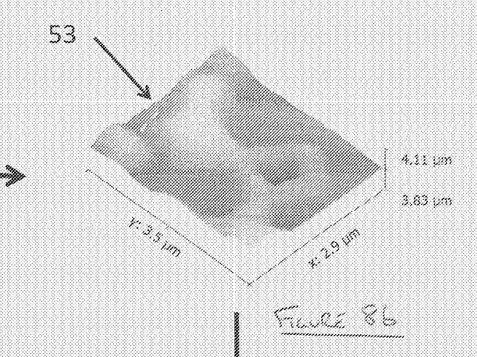
Figure 8C:
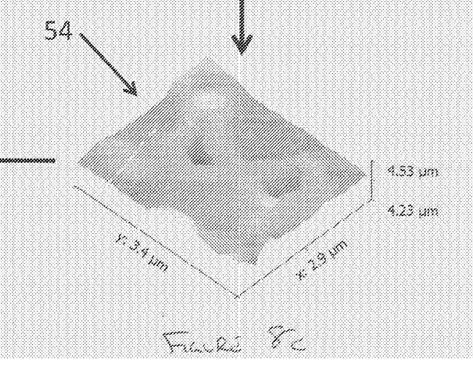
Figure 8D:
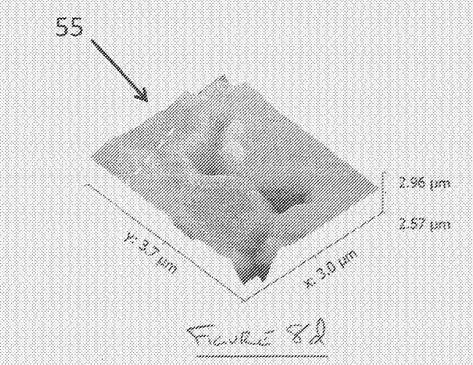
Figures 9, 9A:
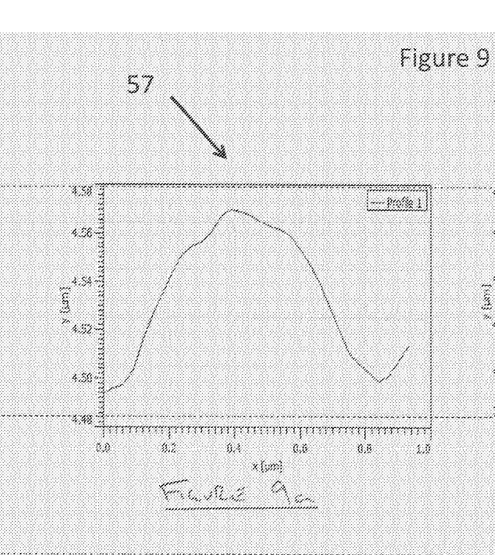
FIGS. 9a-9d. show the results of the line scan highlighted in FIG. 8 whereby a succession of height profiles are produced as the sample is exposed to a series of immersions in a solvent.
Figures 9B, 9C:
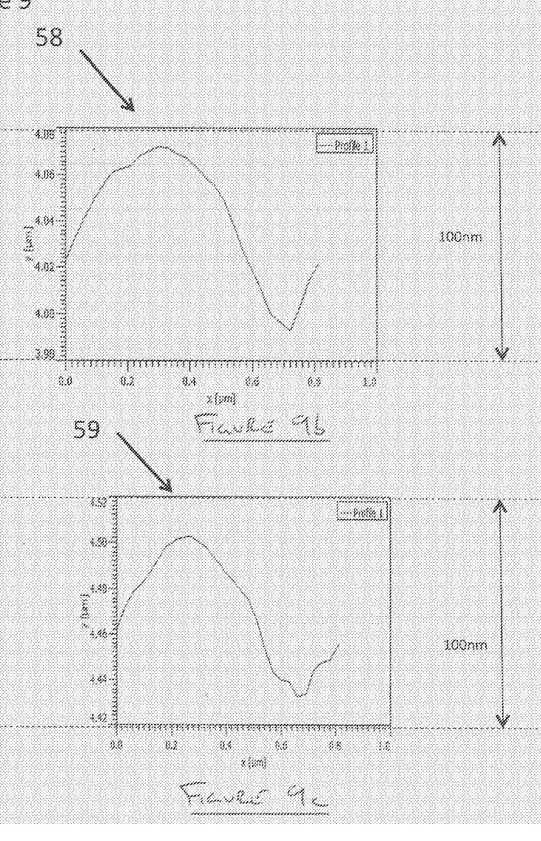
Figure 9D:
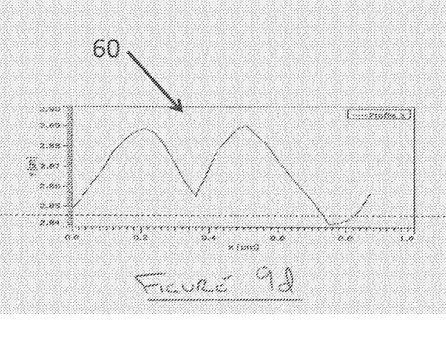
Figure 10:
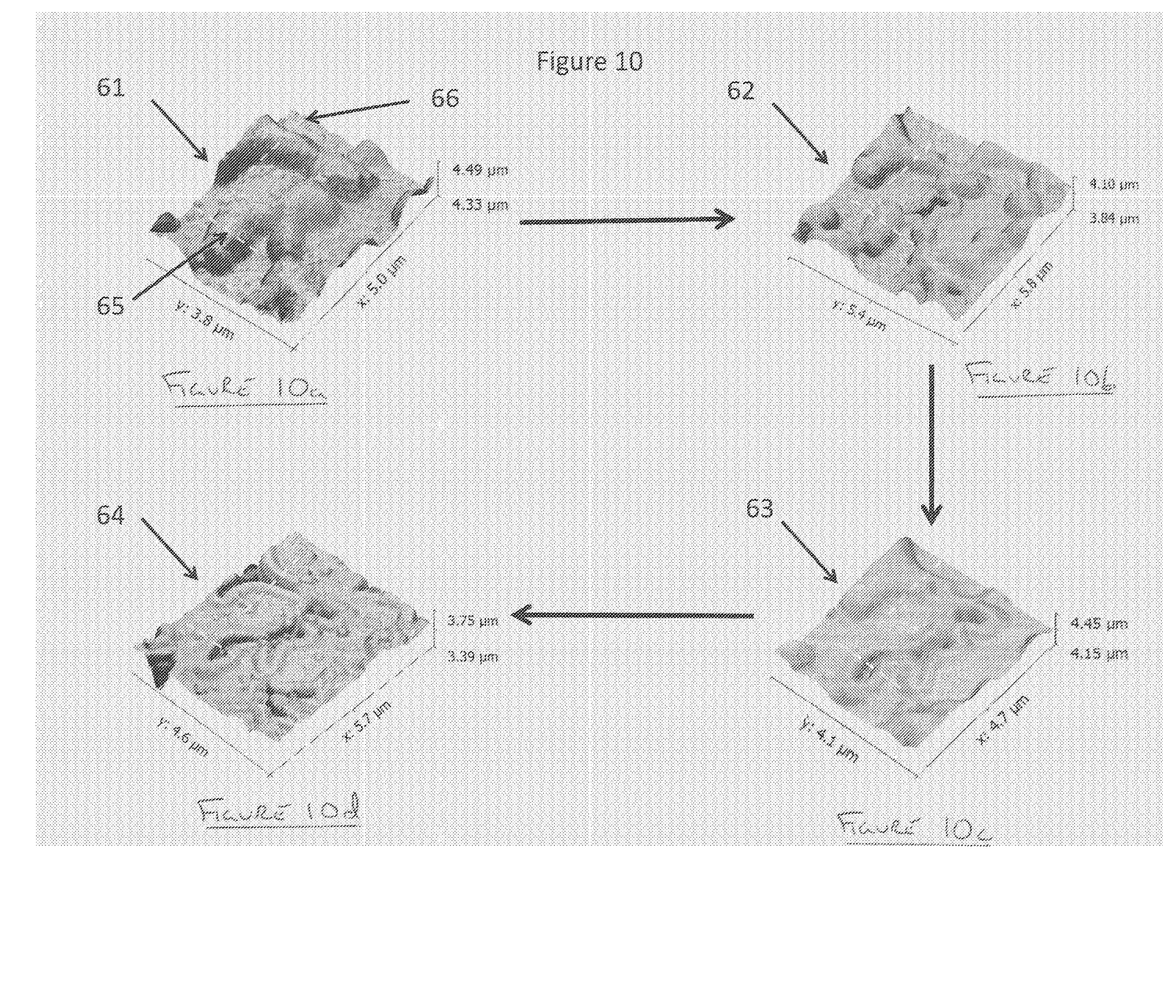
FIGS. 10a-10d show a succession of topographic maps as the sample is exposed to a series of immersions in a solvent according to the areas highlighted in FIG. 5, whereby two line scans over a selected features are illustrated.
Figure 11A:
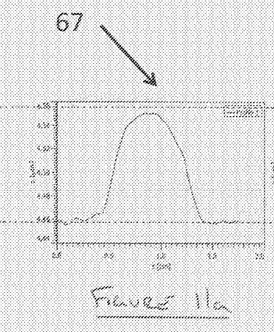
FIGS. 11a-11h shows the results from the two line scans highlighted in FIG. 10 whereby a succession of height profiles are produced as the sample is exposed to a series of immersions in a solvent.
Figures 11B, 11F:
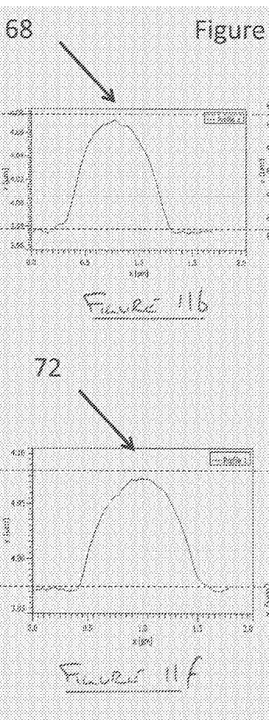
Figure 11C:
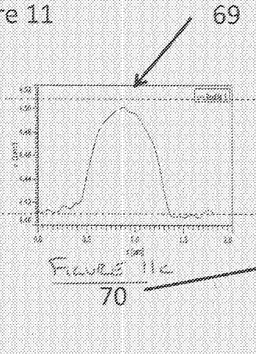
Figures 11D, 11H:
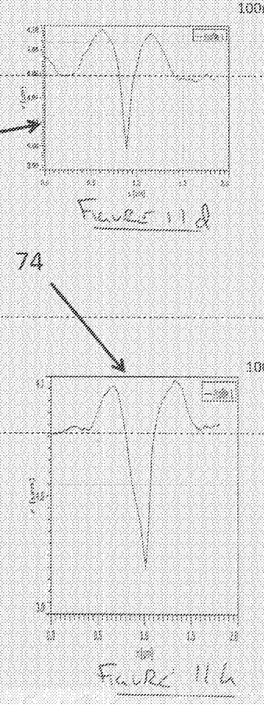
Figure 11E:
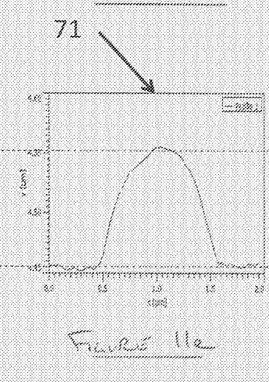
Figure 11G:
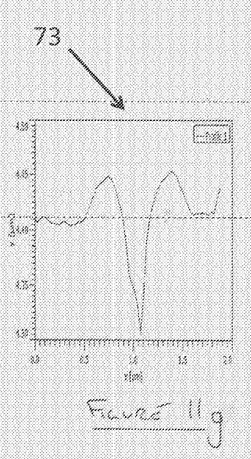

FIGS. 5a and 5b show two maps of the topography obtained with an Atomic Force Microscope (AFM) of the same sample before, 34, and after, 35, exposure to a series of aliquots or pulses of solvent such as can be delivered using the apparatus shown in FIG. 4. It is advantageous to use a sequence of exposures to a solvent or a series of solvents then remove the solvent before imaging with the AFM to avoid damaging the sample while it is very soft due to the action of the solvent.

FIG. 5 shows that there has clearly been a substantial change due to the dissolution of material from the surface. Three areas are selected, before exposure to solvent in FIG. 5a and after exposure to solvent in FIG. 5b; 36 (before)-37 (after), 38 (before)-39 (after) and 40 (before)-41 (after).

FIGS. 6a-6f show the results for area 36-37 for zero exposure 42, one second 43, two seconds 44, four seconds 45, eight seconds 46, and fifteen seconds exposure 47, respectively. A line scan, 48, is selected and this same line scan is obtained for each of the different exposure times. FIGS. 7a-7f show the results of the line scans for the successive exposures 46-51 in the same sequence. It can be seen that there is a 'bump' on the surface that does not greatly diminish until there is an abrupt creation of a hole after eight seconds. FIGS. 8a-8d show the results for area 40-41 for zero exposure 52, one second 53, two seconds 54 and four seconds 55. A line scan, 56, is selected and this same line scan is obtained for each of the different exposure times. FIGS. 9a-9d shows the results of the line scans for the successive exposures 57-59 in the same sequence. It can be seen that there is a 'bump' on the surface that does not greatly diminish until there is an abrupt creation of a hole after four seconds.

FIGS. 10a-10d show the results for area 38-39 for zero exposure 61, one second 62, two seconds 63 and four seconds 64. Two line scans 65, 66, are selected and these same line scans are obtained for each of the different exposure times. FIGS. 11a-11h shows the results of the line scans for the successive exposures 67-70 for line scan 66 and 71-74 for line scan 65 in the same sequence. In the case of line scan 66 it can be seen that there is a 'bump' on the surface that does not greatly diminish until there is an abrupt creation of a hole after two seconds. In the case of line scan 65 it can be seen that there is a 'bump' on the surface that does not greatly diminish until there is an abrupt creation of a hole after one second.

Figure 12:
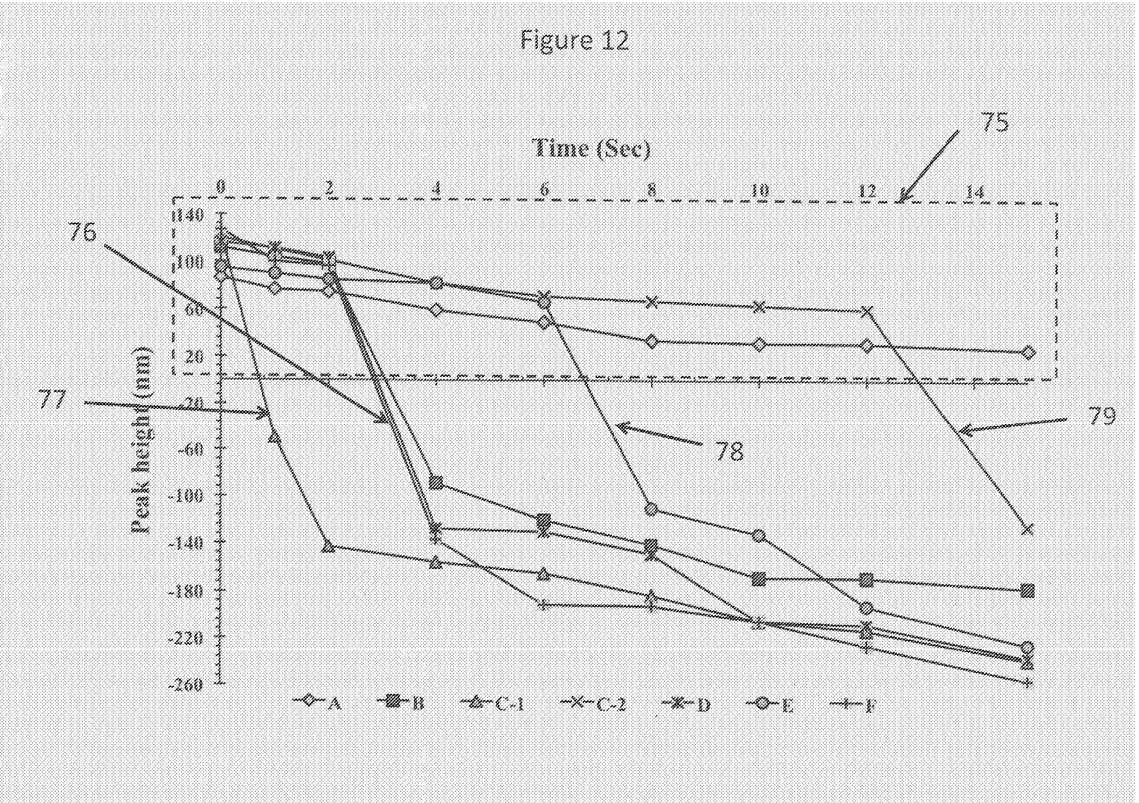
FIG. 12 shows a co-plot of the peak height results of various locations on the sample surface.

A series of results from various locations on the surface are co-plotted in FIG. 12. This illustrates a highly complex combination of solvation, where the height diminishes gradually as seen in the box with dashed lines 75, and erosion, when the hole suddenly appears as seen at 76 to 79. This complex behavior is unexpected and very different from the behavior illustrated in FIG. 2. It can only be characterized using the present invention to remove material a little at a time by successive exposure to aliquots of solvent followed by the removal of the solvent and imaging of the same area each time. In this way the complex and unexpected kinetics of the removal of the soluble phase can be characterized and then correlated with the appearance of material in the aliquots of solvent as illustrated in FIG. 3. Without a full understanding of the complex kinetics for removal of material by the action of the solvent, identification of the chemical nature of the different phases would not be possible.

Figure 13:
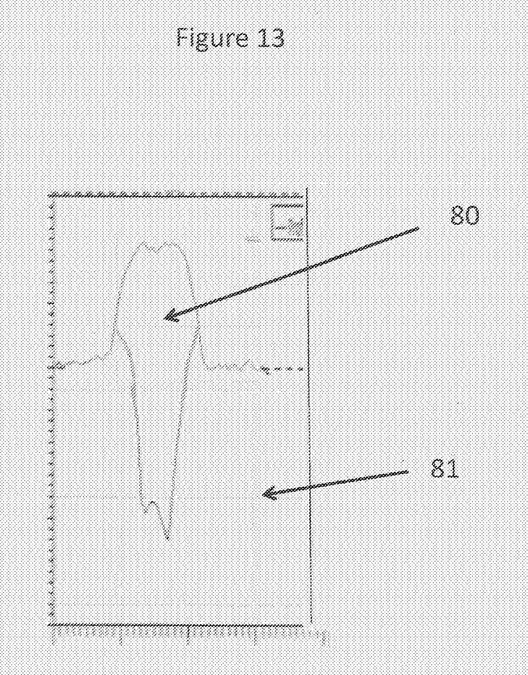
FIG. 13 shows a height plot from a line scan from area highlighted in FIG. 5

The interpretation of these data is that the phase that is presented at zero seconds exposure as a pattern of raised areas as seen in 34 is removed by the solvent while the intervening matrix is dissolved much more slowly. It follows that for each line scan the shape obtained by combining the first and last scan when the process of removal is complete (as determined by applying the invention) provides a cross-section showing the locations of the two phases; this is illustrated in FIG. 13, using line scans 36 and 41. The material in the area 81 Is the highly soluble phase while the surrounding material 82 is less soluble. The chemical nature of the two components can be determined by using conventional analytical methods such as FTIR and HPLC-MS applied to the residue and the aliquots of solvent as illustrated in FIG. 3. By extension, combining the corresponding 3D maps gives a 3D map of the distribution of the two phases.

As such, the present invention includes an apparatus comprising at least one microscope operable to characterize the surface of a sample, at least one conduit to convey a solvent to the sample so that it can dissolve parts of the sample, a pumping system operable to control the composition of a solvent conveyed to the sample, a temperature controlled chamber within which the sample is located, a further conduit to convey the solution away from the sample to at least one instrument capable of analyzing the solutes; the apparatus being arranged to measure changes in the surface of the sample as material is dissolved by the solvent and to analyze the solutes thereby to provide data that can be processed using suitable software to identify the chemical composition of components of the sample and locate their positions within and/or upon the sample even when more than one component dissolves concurrently during the course of the experiment.

Wherein the solution can be conveyed to an instrument capable of analyzing the solutes via the intermediate step of collecting a sequence of aliquots in vessels.

Wherein the solution can be conveyed directly to an instrument that can analyze the solutes.

Wherein the temperature of the sample can be controlled to be an increasing monotonic function of time.

Wherein the temperature of the sample can be controlled to be a combination of a monotonic function of time and a periodic function of time.

Wherein the composition of the solvent can be controlled to be a monotonic function of time.

Wherein the composition of the solvent can be controlled to be a combination of a monotonic function of time and a periodic function of time.

Also a method of identifying the chemical composition of the components of a sample and locating their positions within and/or upon the sample comprising placing the sample within the field of view of a microscope that can characterize changes that occur in a sample as a consequence of its components being dissolved, conveying the solvent to the sample so that it can dissolve parts of the sample, conveying the solution away from the sample, analyzing the solutes, analyzing the images produced by the microscope so that the location and quantity of material dissolved as a function of time are estimated and different components are differentiated on the basis of their dissolution kinetics, correlating the data acquired with the microscope with the analytical data thereby to create a map of how different components of the sample are spatially distributed within and/or upon the sample even when more than one component dissolves concurrently during the course of the experiment Wherein there can be a step of collecting aliquots of the solution for subsequent analysis.

Wherein there can be a step of conveying the solution directly to an instrument capable of analyzing the solutes.

Wherein there can be a parallel experiment that is conducted without the microscope but in substantially the same way with respect to the temperature of the sample, the composition of the solvents and the ratio of the volume of the solvent to the mass of the sample but with a larger sample than that used in the experiment conducted with the microscope; the data obtained by analysing the solutes in the parallel experiment being correlated with the images acquired by the microscope thereby to create a map of how different components of the sample are spatially distributed within and/or upon the sample.

Wherein there can be a step of controlling the temperature of the sample to be an increasing monotonic function of time.

Wherein there can be a step of controlling the temperature of the sample to be a combination of a monotonic function of time and a periodic function.

Wherein there can be a step of controlling the composition of the solvent to change as a monotonic function of time.

Wherein there can be a step of controlling the composition of the solvent to change as a combination of a monotonic function of time and a periodic function.

The invention claimed is:

1. A method of identifying the chemical composition of one or more of the components of a sample and for locating their positions within and/or upon the sample, said method comprising the steps of;
    locating the sample within the field of view of at least one microscope operable to characterize the surface of a sample and suitable for characterizing changes that occur in a sample as a consequence of its components being dissolved,
    conveying at least one fluid solvent to the sample,
    conveying at least part of the solution away from the sample and analysing the solutes;
    using a pump to control the delivery of the fluid solvent to the sample such that its composition is controlled;
    wherein the solvent is delivered as a series of pulses and wherein pulses of solvent separated by air gaps are conveyed to the sample.

2. A method according to claim 1 wherein in the composition of the fluid solvent can be progressively changed.

3. A method of identifying the chemical composition of one or more of the components of a sample and for locating their positions within and/or upon the sample said method comprising the steps of;
    locating the sample within the field of view of at least one microscope operable to characterize the surface of a sample and suitable for characterizing changes that occur in a sample as a consequence of its components being dissolved,
    conveying at least one fluid solvent to the sample,
    conveying at least part of the solution away from the sample and analysing the solutes;
    using a pump to control the delivery of the fluid solvent to the sample such that its composition is controlled;
    wherein pulses of different solvents separated by an air gap are conveyed to the sample characterised in that pump controls the composition of the solvent delivered to the sample by mixing the content of two or more reservoirs.

* * * * *